(12) United States Patent
del Rio et al.

(10) Patent No.: US 10,952,747 B2
(45) Date of Patent: Mar. 23, 2021

(54) CUTTING BURR SHANK CONFIGURATION

(71) Applicant: DePuy Synthes Products, Inc., Raynham, MA (US)

(72) Inventors: Eddy H. del Rio, West Palm Beach, FL (US); Duane Jeffrey Enck, West Palm Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 165 days.

(21) Appl. No.: 16/222,446

(22) Filed: Dec. 17, 2018

(65) Prior Publication Data
US 2019/0223888 A1    Jul. 25, 2019

Related U.S. Application Data

(63) Continuation of application No. 15/818,314, filed on Nov. 20, 2017, now Pat. No. 10,154,849, which is a
(Continued)

(51) Int. Cl.
*A61B 17/16*    (2006.01)
(52) U.S. Cl.
CPC ........ *A61B 17/1617* (2013.01); *A61B 17/162* (2013.01); *Y10T 408/907* (2015.01)
(58) Field of Classification Search
CPC ... A61B 17/16; A61B 17/1615; A61B 17/162; Y10T 408/907
USPC ....... 606/79–81, 84, 85, 167, 169–171, 180; 81/177.85, 438; 279/35, 37, 77, 78, 89, 279/106, 107, 131, 156; 403/383; 408/226
See application file for complete search history.

(56) References Cited

U.S. PATENT DOCUMENTS 170,604 A    11/1875    Williams
170,694 A    12/1875    Williams
(Continued)

FOREIGN PATENT DOCUMENTS

CN    2631675    3/2003
CN    1406700    4/2003
(Continued)

OTHER PUBLICATIONS

Office Action, dated Dec. 16, 2014, received in connection with JP Patent Application No. 2014503639. (English Translation).
(Continued)

*Primary Examiner* — Eric S Gibson
(74) *Attorney, Agent, or Firm* — Meunier Carlin & Curfman LLC

(57) ABSTRACT

A cutting burr that includes a pair of axially spaced diamond-shaped portions designed to be keyed into a spindle of a locking mechanism of a high speed surgical drilling instrument and adapted to fit into a single pawl thereof to lock said cutting burr in place so as to prevent axial movement thereof and provide concentric rotation of said cutting burr without any wobbling. The orientation of both portions may be identical with respect to a center plan and diamond shape in the portion at the proximal end of the shank of the cutting tool may be larger than the intermediately located diamond shape of the other portion. The apexes of the facets of the six-sided diamond shape may be disposed below the surface of the shank of the cutting burr.

19 Claims, 3 Drawing Sheets

Related U.S. Application Data continuation of application No. 15/225,043, filed on Aug. 1, 2016, now Pat. No. 9,820,756, which is a continuation of application No. 14/223,011, filed on Mar. 24, 2014, now Pat. No. 9,402,638, which is a continuation of application No. 13/082,016, filed on Apr. 7, 2011, now Pat. No. 8,690,876.

(56) References Cited

U.S. PATENT DOCUMENTS

| | | | | |
|---|---|---|---|---|
| RE8,360 | E | 8/1878 | Williams | |
| 233,707 | A * | 10/1880 | Starr | B23B 31/103 279/77 |
| 233,709 | A | 10/1880 | Starr | |
| 269,627 | A * | 12/1882 | Bonner | B23G 1/22 470/58 |
| 283,745 | A * | 8/1883 | Bartlett | B23B 39/00 408/65 |
| 287,683 | A | 10/1883 | Johnston et al. | |
| 302,870 | A * | 7/1884 | Starr | A61C 1/141 433/128 |
| 327,558 | A * | 10/1885 | Kuder | B44B 3/065 81/4 |
| 359,798 | A * | 3/1887 | Mann | B23B 31/18 279/35 |
| 415,983 | A | 11/1889 | Starr | |
| 418,108 | A | 12/1889 | Browne | |
| 474,011 | A | 5/1892 | Harrison | |
| 553,226 | A * | 1/1896 | Brockett | B23B 31/18 279/35 |
| 748,398 | A * | 12/1903 | Middleton | B23B 51/123 279/103 |
| 988,154 | A * | 3/1911 | Thiemer | B23D 43/02 407/16 |
| 988,903 | A * | 4/1911 | Smith | B23B 31/005 408/226 |
| 1,135,057 | A * | 4/1915 | Schultis | B23G 5/12 408/74 |
| 1,188,533 | A * | 6/1916 | Cobey | B23B 31/1246 279/63 |
| 1,433,590 | A * | 10/1922 | Ziegler | B23G 1/46 279/35 |
| 1,503,962 | A * | 8/1924 | Milliken | B24B 19/03 65/61 |
| 1,578,397 | A | 3/1926 | Cone | |
| 1,717,663 | A | 6/1929 | Checkley | |
| 1,726,012 | A * | 8/1929 | Bilz | B25C 1/02 227/147 |
| 1,862,337 | A * | 6/1932 | Emrick | B23B 31/028 279/90 |
| 1,947,957 | A * | 2/1934 | Tiliman | B23B 31/185 279/106 |
| 2,012,280 | A * | 8/1935 | Johansen | E21B 3/04 279/35 |
| 2,101,347 | A * | 12/1937 | Robinette | B23G 5/064 408/222 |
| 2,367,863 | A * | 1/1945 | Grey | B23B 31/14 279/50 |
| 2,390,950 | A * | 12/1945 | Lanfranconi | B23B 31/005 408/226 |
| 2,405,018 | A * | 7/1946 | Crowley | B21D 51/36 294/106 |
| 2,448,817 | A * | 9/1948 | McArthur | F16B 9/02 403/321 |
| 2,473,380 | A * | 6/1949 | Ljunggren | B23B 31/32 279/139 |
| 2,494,166 | A * | 1/1950 | Drissner | B23B 31/18 279/106 |
| 2,543,290 | A * | 2/1951 | Johansson | B23B 31/223 279/78 |
| 2,614,781 | A * | 10/1952 | Engel | A47B 91/08 248/502 |
| 2,686,682 | A * | 8/1954 | Csaki | B23B 31/201 279/51 |
| 2,740,974 | A * | 4/1956 | Lazarus | B23G 5/064 408/222 |
| 2,769,643 | A * | 11/1956 | Berthold | B23B 31/201 279/50 |
| 2,787,010 | A * | 4/1957 | Uphoff | B23G 5/06 408/204 |
| 2,874,985 | A * | 2/1959 | March | B23Q 3/12 403/258 |
| 2,939,643 | A * | 6/1960 | Barsam, Jr. | G03B 21/43 242/545 |
| 2,955,831 | A * | 10/1960 | Zandberg | A61C 1/142 279/78 |
| 3,046,029 | A | 7/1962 | Weber et al. | |
| 3,054,308 | A * | 9/1962 | Larry | B23B 51/0486 408/59 |
| 3,084,898 | A * | 4/1963 | Miller | F16K 31/122 251/1.1 |
| 3,136,347 | A * | 6/1964 | Linquist | B23B 31/005 408/226 |
| RE25,804 | E | 6/1965 | Misuraca | |
| 3,252,667 | A * | 5/1966 | Miller | H01F 41/06 242/571.6 |
| 3,466,971 | A * | 9/1969 | Meyer | B23Q 3/15553 409/233 |
| 3,533,638 | A * | 10/1970 | Sedgwick | B23B 31/103 279/89 |
| 3,574,374 | A * | 4/1971 | Keller | A61C 1/18 403/4 |
| 3,589,826 | A * | 6/1971 | Fenn | B23B 31/12 408/226 |
| 3,596,917 | A * | 8/1971 | Meyer | B23B 31/18 279/89 |
| 3,599,996 | A * | 8/1971 | Holt | B23B 31/18 279/37 |
| 4,032,163 | A * | 6/1977 | Holt | B23B 31/18 279/37 |
| 4,055,185 | A * | 10/1977 | Waldron | A61B 17/1633 606/180 |
| 4,073,497 | A | 2/1978 | Flagg | |
| 4,114,276 | A * | 9/1978 | Malata | A61C 1/14 279/145 |
| 4,115,024 | A | 9/1978 | Süssmuth | |
| 4,131,165 | A * | 12/1978 | Wanner | B23Q 3/12 173/133 |
| 4,298,074 | A * | 11/1981 | Mattchen | A61B 17/1624 173/129 |
| 4,303,252 | A * | 12/1981 | Snider | B23B 31/18 279/106 |
| 4,325,661 | A | 4/1982 | Tickins | |
| 4,374,481 | A * | 2/1983 | Brodie | B25B 13/44 279/107 |
| 4,565,472 | A * | 1/1986 | Brennsteiner | B23B 31/005 408/226 |
| 4,632,195 | A * | 12/1986 | Emmerich | E21B 17/046 175/320 |
| 4,710,075 | A * | 12/1987 | Davison | A61B 17/16 33/512 |
| 4,984,667 | A | 1/1991 | Tjaden | |
| 5,037,251 | A * | 8/1991 | Roth | B23B 31/005 408/222 |
| 5,074,025 | A * | 12/1991 | Willard | B23B 31/005 279/103 |
| 5,152,642 | A | 10/1992 | Pitts et al. | |
| 5,218,890 | A | 6/1993 | Christ, Jr. | |
| 5,271,697 | A * | 12/1993 | Johnson | B23B 31/1071 279/75 |
| 5,421,682 | A * | 6/1995 | Obermeier | B25D 17/088 279/19.3 |
| 5,433,562 | A * | 7/1995 | Phillips | B23B 31/261 279/125 |
| 5,466,101 | A * | 11/1995 | Meyen | B25D 17/088 279/19.4 |
| 5,542,846 | A * | 8/1996 | Quinn | A61C 1/141 279/106 |

(56) References Cited

U.S. PATENT DOCUMENTS

| | | | |
|---|---|---|---|
| 5,601,560 A * | 2/1997 | Del Rio | A61B 17/162 408/231 |
| 5,630,818 A * | 5/1997 | Del Rio | A61B 17/162 279/77 |
| 5,658,305 A | 8/1997 | Baker | |
| 5,664,792 A * | 9/1997 | Tseng | B23B 31/103 16/422 |
| 5,735,535 A * | 4/1998 | McCombs | A61B 17/162 279/131 |
| 5,741,263 A * | 4/1998 | Umber | A61B 17/162 279/75 |
| 5,820,136 A * | 10/1998 | Han | B23B 31/14 279/131 |
| 5,833,246 A | 11/1998 | Trott | |
| 5,833,704 A | 11/1998 | McCombs et al. | |
| 5,888,200 A * | 3/1999 | Walen | A61B 17/1622 606/167 |
| 5,904,687 A * | 5/1999 | Del Rio | A61B 17/162 408/231 |
| 5,921,563 A * | 7/1999 | Huggins | B23B 31/14 279/131 |
| 5,941,891 A * | 8/1999 | Walen | A61B 17/1622 606/167 |
| 5,957,634 A | 9/1999 | Carpinetti | |
| 6,033,408 A * | 3/2000 | Gage | A61B 17/162 173/218 |
| 6,045,564 A * | 4/2000 | Walen | A61B 17/1622 606/1 |
| 6,129,363 A * | 10/2000 | Mack | B23B 31/1215 279/158 |
| 6,135,461 A | 10/2000 | Below et al. | |
| RE37,358 E * | 9/2001 | Del Rio | A61B 17/162 408/231 |
| 6,302,408 B1 | 10/2001 | Zierpka | |
| 6,341,926 B1 * | 1/2002 | Liu | B23B 31/005 408/222 |
| 6,409,181 B1 | 6/2002 | Hsueh | |
| 6,533,235 B1 * | 3/2003 | Dymerski | B60N 2/0232 248/421 |
| 6,533,291 B2 * | 3/2003 | Huggins | B23B 31/1238 279/137 |
| 6,572,311 B2 * | 6/2003 | Vasudeva | B23B 31/005 408/226 |
| 6,607,533 B2 * | 8/2003 | Del Rio | A61B 17/162 408/226 |
| 6,623,220 B2 | 9/2003 | Nuss et al. | |
| 6,705,807 B1 * | 3/2004 | Rudolph | B23B 51/0426 279/143 |
| 6,725,749 B1 * | 4/2004 | Liou | B25B 23/0035 81/438 |
| 6,733,218 B2 * | 5/2004 | Del Rio | A61B 17/162 279/79 |
| 6,769,846 B2 | 8/2004 | Campbell, Jr. et al. | |
| 6,780,189 B2 * | 8/2004 | Tidwell | A61B 17/162 606/170 |
| 7,011,661 B2 * | 3/2006 | Riedel | A61B 17/162 606/170 |
| 7,028,589 B1 * | 4/2006 | Cheng | B25B 23/0035 81/125 |
| 7,066,940 B2 * | 6/2006 | Riedel | A61B 17/162 606/167 |
| 7,114,728 B2 * | 10/2006 | Chen | B23B 31/107 279/24 |
| 7,140,817 B1 * | 11/2006 | Phillips | B23B 31/008 409/182 |
| 7,207,400 B2 * | 4/2007 | Bise | E21B 17/03 175/320 |
| 7,258,349 B2 * | 8/2007 | Frauhammer | B23Q 3/12 279/19 |
| 7,316,529 B2 * | 1/2008 | Phillips | B23B 31/008 144/136.95 |
| 7,367,762 B2 | 5/2008 | Takase et al. | |
| 7,465,309 B2 | 12/2008 | Walen | |
| 7,712,746 B2 * | 5/2010 | Manschitz | B23Q 3/12 279/37 |
| 7,845,428 B2 * | 12/2010 | Sakamaki | B23B 31/1071 173/164 |
| 8,273,097 B2 * | 9/2012 | Malla | A61M 3/0229 606/167 |
| 8,403,338 B2 * | 3/2013 | Hangleiter | B23B 31/265 279/37 |
| 8,690,876 B2 * | 4/2014 | del Rio | A61B 17/1617 606/80 |
| 8,801,713 B2 * | 8/2014 | del Rio | A61B 17/1617 606/80 |
| 9,113,917 B2 * | 8/2015 | del Rio | A61B 17/1615 |
| 9,381,023 B2 | 7/2016 | del Rio et al. | |
| 9,402,638 B2 * | 8/2016 | del Rio | A61B 17/162 |
| 9,681,879 B2 | 6/2017 | del Rio et al. | |
| 9,820,756 B2 | 11/2017 | del Rio et al. | |
| 10,154,849 B2 | 12/2018 | del Rio et al. | |
| 10,194,921 B2 | 2/2019 | del Rio et al. | |
| 2001/0006280 A1 * | 7/2001 | Hangleiter | B24B 45/00 279/37 |
| 2001/0042964 A1 * | 11/2001 | Bedi | B25B 15/001 279/30 |
| 2002/0009341 A1 | 1/2002 | Vasudeva | |
| 2002/0058958 A1 * | 5/2002 | Walen | A61B 17/32002 606/170 |
| 2002/0151902 A1 * | 10/2002 | Riedel | A61B 17/162 606/80 |
| 2002/0159850 A1 | 10/2002 | Ravid | |
| 2002/0165549 A1 * | 11/2002 | Owusu-Akyaw | A61B 17/1628 606/80 |
| 2003/0060829 A1 * | 3/2003 | Del Rio | A61B 17/162 606/80 |
| 2003/0060841 A1 * | 3/2003 | Del Rio | A61B 17/162 606/167 |
| 2003/0130663 A1 * | 7/2003 | Walen | A61B 17/32002 606/80 |
| 2003/0163134 A1 * | 8/2003 | Riedel | A61B 17/32002 606/79 |
| 2005/0096661 A1 * | 5/2005 | Farrow | A61B 50/30 606/79 |
| 2006/0049587 A1 | 3/2006 | Cornwell | |
| 2006/0053974 A1 | 3/2006 | Blust et al. | |
| 2008/0119863 A1 * | 5/2008 | Mellier | A61B 17/0469 606/99 |
| 2008/0208195 A1 | 8/2008 | Shores et al. | |
| 2008/0208229 A1 * | 8/2008 | Tidwell | A61B 17/1628 606/167 |
| 2009/0146421 A1 | 6/2009 | Engdahl | |
| 2009/0273146 A1 * | 11/2009 | Dezheng | B23D 51/10 279/78 |
| 2009/0326540 A1 * | 12/2009 | Estes | A61B 17/144 606/82 |
| 2010/0063524 A1 * | 3/2010 | McCombs | A61B 17/32002 606/167 |
| 2010/0219594 A1 * | 9/2010 | Nash | B25B 23/0035 279/77 |
| 2012/0003057 A1 * | 1/2012 | Leyba | B23B 31/005 408/226 |
| 2012/0259336 A1 * | 10/2012 | del Rio | A61B 17/1617 606/80 |
| 2012/0259337 A1 * | 10/2012 | del Rio | A61B 17/1615 606/80 |
| 2012/0275875 A1 * | 11/2012 | Gischus | B23G 5/064 408/226 |
| 2013/0130663 A1 | 5/2013 | Jung et al. | |
| 2015/0032111 A1 * | 1/2015 | del Rio | A61B 17/1615 606/80 |
| 2019/0223888 A1 * | 7/2019 | del Rio | A61B 17/1617 |

FOREIGN PATENT DOCUMENTS

| | | |
|---|---|---|
| CN | 1672641 | 9/2005 |
| CN | 2774405 | 4/2006 |

(56) References Cited

FOREIGN PATENT DOCUMENTS

| | | | | |
|---|---|---|---|---|
| CN | 2882550 | | 3/2007 | |
| CN | 101365390 | | 2/2009 | |
| JP | 02009507 | | 1/1990 | |
| JP | 02009507 A | * | 1/1990 | |
| JP | 03019703 | | 1/1991 | |
| JP | 03019703 A | * | 1/1991 | ........... B23B 31/261 |
| JP | 07214406 | | 8/1995 | |
| JP | 07214406 A | * | 8/1995 | ........... B25D 17/088 |
| JP | 2000/052114 | | 2/2000 | |
| JP | 2000052114 A | * | 2/2000 | ........... B25D 17/088 |
| JP | 2002/137111 | | 5/2002 | |
| JP | 2002137111 A | * | 5/2002 | ......... B23B 51/0473 |
| JP | 2011/136530 | | 7/2011 | |
| WO | 1996/010962 | | 4/1996 | |
| WO | 2004/082490 | | 9/2004 | |
| WO | 2008/020828 | | 2/2008 | |
| WO | WO-2008020828 A2 | * | 2/2008 | ......... B23B 31/1071 |
| WO | 2012/138338 | | 10/2012 | |

OTHER PUBLICATIONS

International Preliminary Report on Patentability and Written Opinion, dated Oct. 8, 2013, received in connection with corresponding International Patent Application No. PCT/US2011/031505.

International Search Report, dated Feb. 28, 2012, received in connection with corresponding International Patent Application No. PCT/US2011/031505.

International Preliminary Report on Patentability and Written Opinion, dated Oct. 8, 2013, received in connection with related International Patent Application No. PCT/US2011/031512.

International Search Report, dated Jan. 4, 2012, received in connection with related International Patent Application No. PCT/US2011/031512.

* cited by examiner

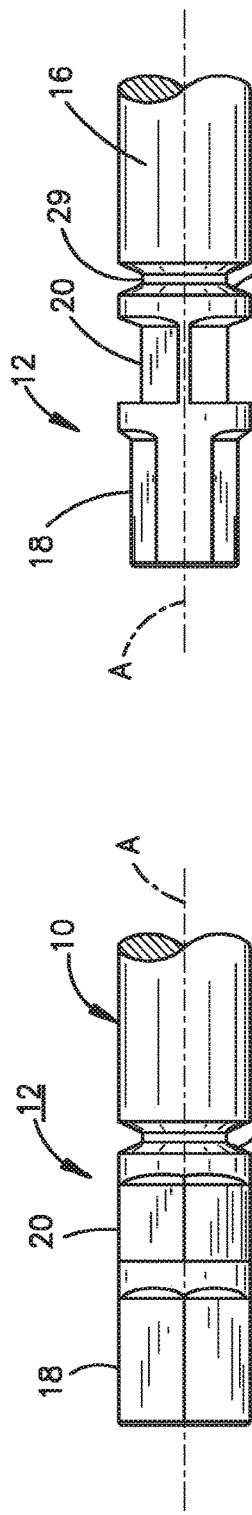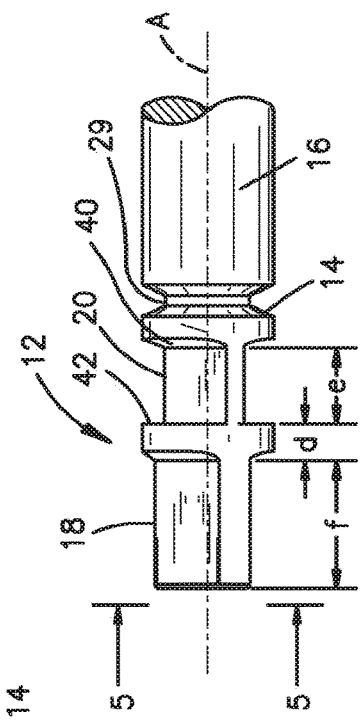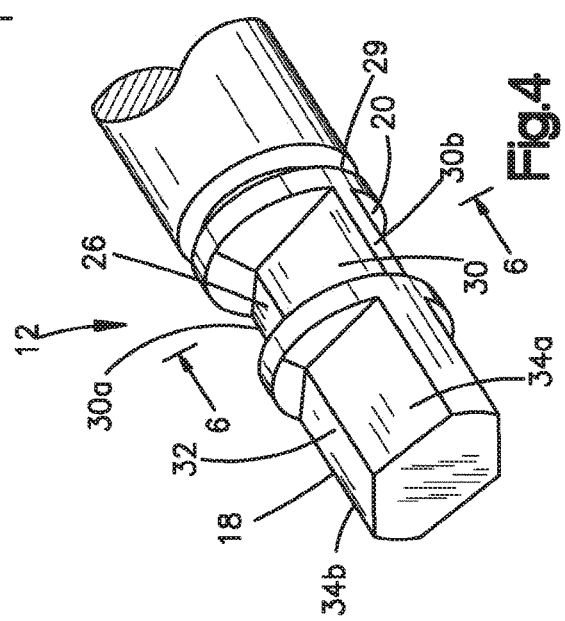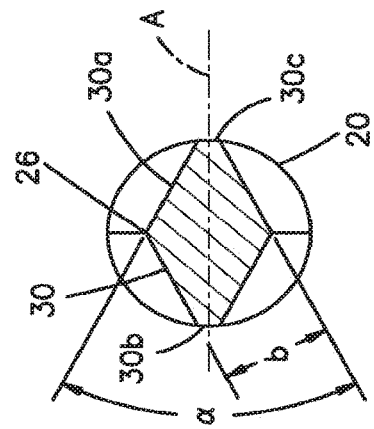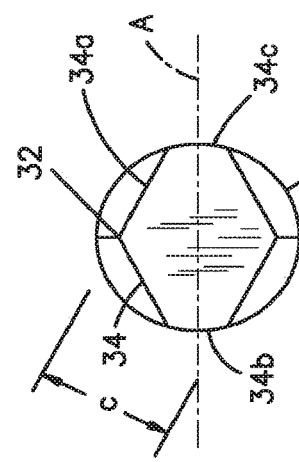

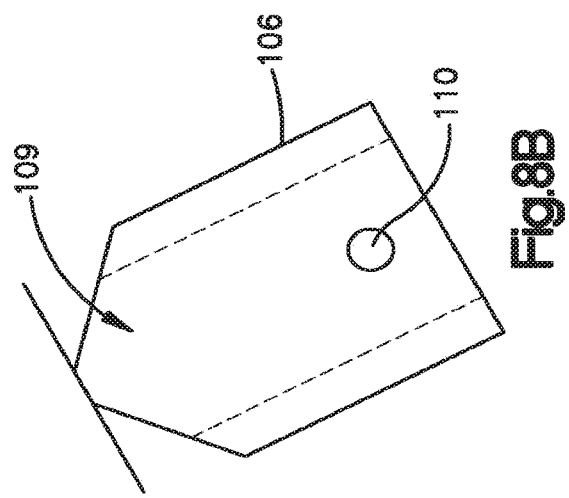
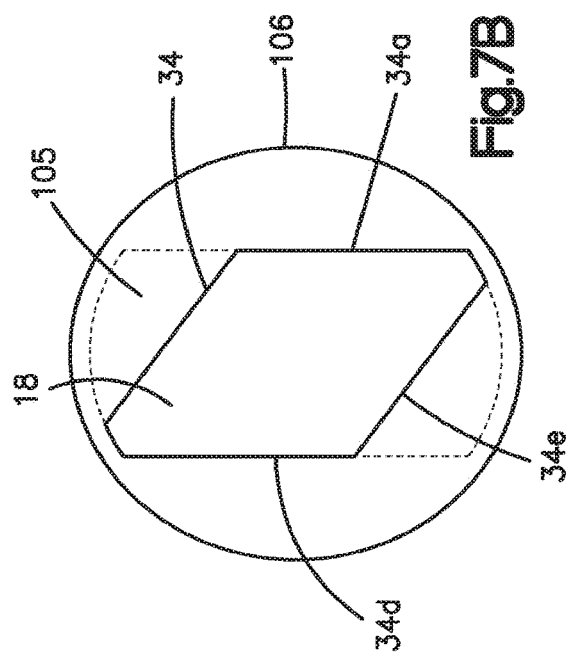
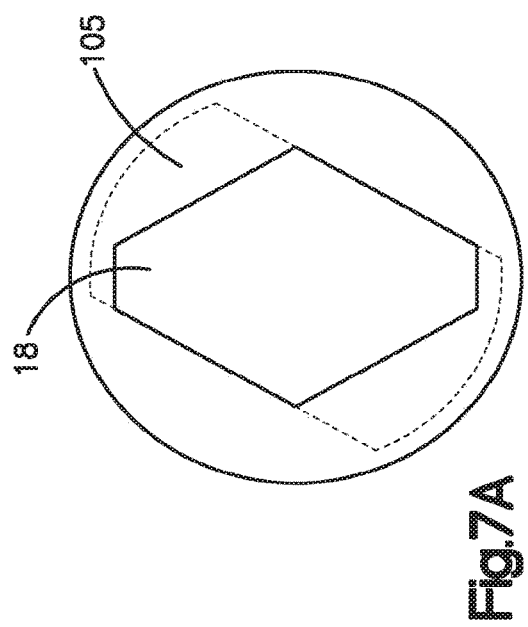
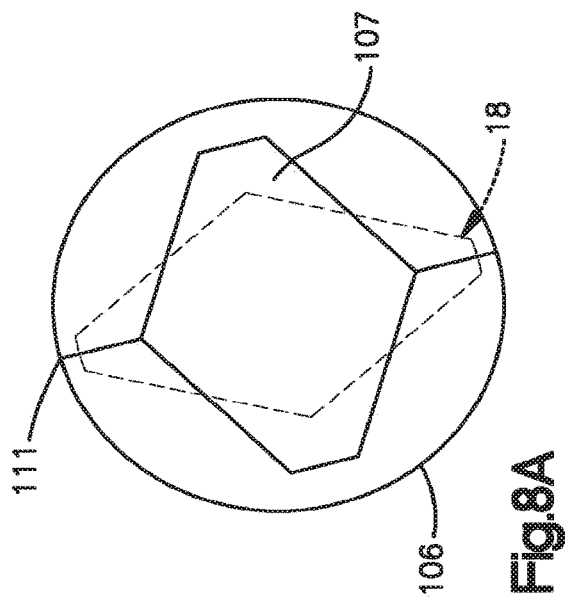

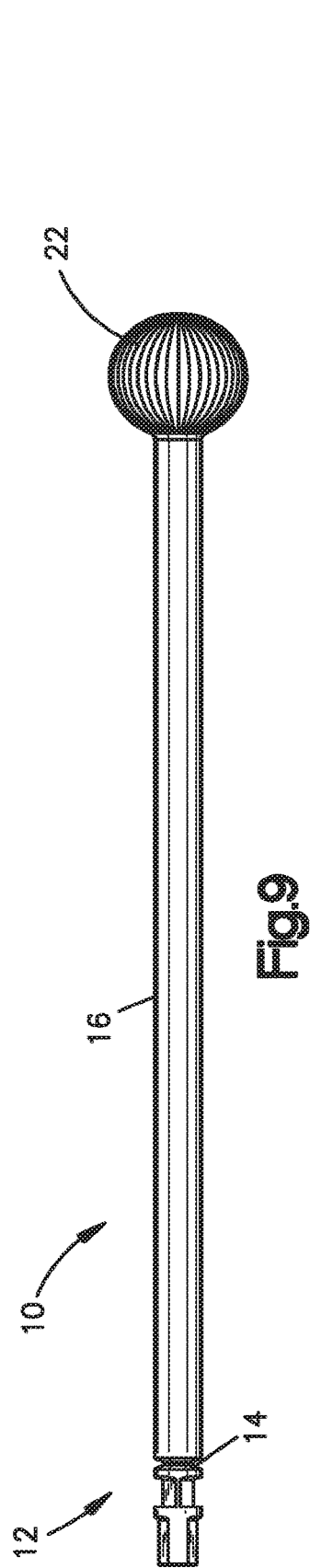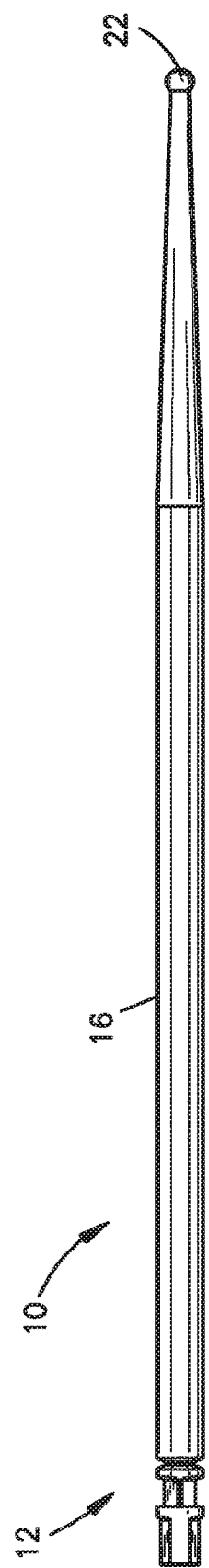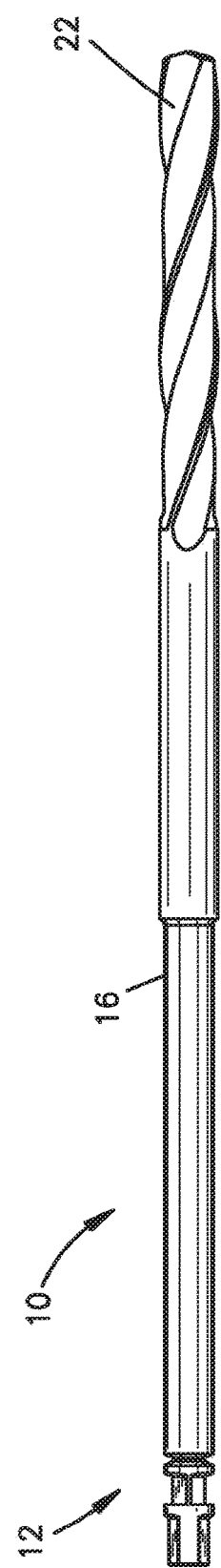

CUTTING BURR SHANK CONFIGURATION

CROSS-REFERENCE TO RELATED APPLICATIONS

The subject matter described in this application is related to subject matter disclosed in the following commonly assigned applications: U.S. patent application Ser. No. 15/818,314 filed Nov. 20, 2017, which is a continuation of U.S. patent application Ser. No. 15/225,043 (now U.S. Pat. No. 9,820,756) filed Aug. 1, 2016, which is a continuation of U.S. patent application Ser. No. 14/223,011 (now U.S. Pat. No. 9,402,638) filed Mar. 24, 2014, which is a continuation of U.S. patent application Ser. No. 13/082,016 (now U.S. Pat. No. 8,690,876), filed on Apr. 7, 2011, entitled "CUTTING BURR SHANK CONFIGURATION," which are incorporated herein by reference in their entirety.

BACKGROUND

When performing surgery, surgeons may utilize a surgical drilling instrument for drilling, cutting or shaping bones that utilize a numerous different kinds and sizes of cutting burrs and attachments. During certain medical operations, the cutting burr needs to be changed. The change must be done timely and efficiently in view of the surgical demands. To this end, the portion of the cutting burr, namely, the proximate end of the shank typically lacks a configuration to accommodate this change of the cutting burr.

SUMMARY

Disclosed herein is a cutting burr that provides for a quick release that is fast and simple, and which facilitates the insertion of the cutting burr into a surgical drilling instrument. The cutting burr may have a pair of axially spaced six sided diamond-shaped portions, where one diamond-shaped portion may be formed at an edge of the proximal end of the cutting burr and provides a positive connection with a drive spindle that is connected to a drive motor of the surgical drilling instrument. A second, axially disposed diamond-shaped portion is adapted to mate with a locking pawl of the surgical drilling instrument. The locking pawl engages the axially disposed diamond-shaped portion to lock the cutting burr into the surgical drilling instrument with substantially no axial movement.

In some implementations, a detent pawl is provided to hold the cutting burr within the surgical instrument when it is in a loading position. The detent pawl may engage the axially disposed diamond-shaped portion at a side opposite the locking pawl.

In some implementations, the diamond-shaped portion at the proximal end is sized such that it can be used with older surgical drilling instruments that may not be provided with a complementary receiving recess for the diamond-shaped portion.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary is better understood when read in conjunction with the appended drawings. For the purposes of illustration, there is shown in the drawings exemplary implementations; however, these implementations are not limited to the specific methods and instrumentalities disclosed. In the drawings:

FIG. 1 a fragmentary top plan view illustrating the axially spaced six-sided diamond-shaped cut out portion or portions formed on the proximate end of the shank of the cutting burr;

FIG. 2 is a perspective view of FIG. 1;

FIG. 3 is another prospective view of FIG. 1 slightly turned illustrating one of the facets in each of the six-sided diamond-shaped portions;

FIG. 4 is another perspective view of FIG. 2 slightly turned illustrating the top facets of the six-sided diamond-shaped portions;

FIG. 5 is an end view taken along lines 5-5 of FIG. 3 illustrating the shape of the six-sided diamond-shaped portion formed in the cutting burr shank;

FIG. 6 is a sectional view taken along lines 6-6 of FIG. 4 illustrating the shape of the six-sided diamond-shaped portion and illustrating the different sizes and the orientation of the six-sided diamond portion formed in the cutting burr shank;

FIGS. 7A and 7B illustrate a backwards compatibility of the cutting burr of FIGS. 1-6 within a receiving portion of conventional surgical drill;

FIGS. 8A and 8B illustrate a self-alignment aspect of the diamond-shaped portion at a proximal end of the cutting burr in relation to a keyed slot of a surgical drill;

FIG. 9 is an elevated view of the cutting burr with a spherical shaped cutting bit illustrating the diamond-shaped portions formed in the shank thereof;

FIG. 10 is another elevated view of an example cutting burr; and

FIG. 11 is another elevated view of an example cutting burr.

DETAILED DESCRIPTION

As used herein, the term "cutting burr" may be analogous with terms such as bit, drill bit, surgical drill bit and the like. The term "attachment" may have several meanings within the text of this application, but when generalized as a component of a surgical drilling instrument it refers to a portion of the instrument that attaches to the end of the motor/locking mechanism and receives the cutting burr. An "attachment" may be a controlled depth attachment, a minimally invasive attachment and the like. The surgical drilling instrument may include an integral motor (electric or pneumatic) and a locking mechanism and an attachment releasably connected to the locking mechanism.

High speed surgical drills are increasingly being used by surgeons when performing delicate bone dissection in areas such as the cervical and lumbar spine. Such surgical drills operate at very high R.P.M., and are able to rotationally drive multiple types of attachments and cutting burrs. As will be described below, a cutting burr of the present disclosure includes a shank that defines two substantially diamond-shaped portions. The substantially diamond-shaped portions provide for ease of insertion and removal of the cutting burr to and from a compatible surgical drill. The substantially diamond-shaped portions also enable the surgical drill to direct higher levels of torque to the cutting burr during surgical procedures.

Referring to FIGS. 1-6, the cutting burr is generally illustrated by reference numeral 10. The attachment portion 12 of the shank 16 of the cutting burr 10 is generally shown as reference numeral 12. A proximal end 14 of the shank 16 is formed with a pair of axially spaced six-sided diamond-shaped portions 18 and 20. As shown in FIGS. 4 and 5, an upper surface of portion 18 includes an apex 32 and a pair of facets 34 and 34a also fairing to side edges 34b and 34c. The side edges 34b and 34c may be curved to match the radius of curvature of an outer surface of the shank 16. As shown in FIGS. 4 and 6, an upper surface 24 of the portion 20 includes apex 26 and a pair of facets 30 and 30a fairing from the apex 26 to the side edges 30b and 30c. The side edges 30b and 30c may be curved to match the radius of curvature of an outer surface of the shank 16.

As shown in the Figs. the diametrical dimensions of the vertices in both portions is less than the diameter of the main body of the shank. The shank 16 may include an annular groove 29. The lower surfaces of the pair of six-sided diamond portions 18 and 20 are a mirror image of the upper surface. While the diamond-shaped portions 18 and 20 are described as being "diamond-shaped," it is noted that such terminology is intended to encompass any six-sided (hexagon) shape having a cross-section with flat edges that meet at a six vertices, curved edges that meet at six points, or some combination of both to form the six sides. The flat and curved edges, and combinations thereof, may be applied to other polygon shapes having different numbers of sides.

The diamond-shaped portion 18 at the outermost proximal end is designed to be inserted into a mating drive portion of a surgical drill, as will be described with reference to FIGS. 8A and 8B. The diamond-shaped portion 20 is provided as an abutment surface of a retractable locking pawl of the surgical drill to provide axial locking of the shank 16 within the surgical drill. The locking pawl may axially abut the adjacent abutment surface of the diamond-shaped portion 20 to axially lock the cutting burr 10 in place, thus providing substantially zero axial movement. For example, an engagement portion of locking pawl may be contoured having a generally V-shape with inner surfaces that fit against the facets 30 and 30a of the diamond-shaped portion 20.

As shown in FIG. 3, a back wall 42 may be formed perpendicular with relation to the central line A and faces a front wall 40 that is tapered from the facet (e.g., 30a) to the outside diameter of the shank 16. In accordance with some aspects, an engagement face of the locking pawl may abut against the back wall 42 to provide axial locking of the cutting burr 10 within the surgical drill. A tapered front wall 40 may facilitate the engagement of the locking pawl into the diamond-shaped portion 20.

The diamond-shaped portion 20 may also be engaged by a detent pawl of the surgical drill. For example, an engagement end of detent pawl may be contoured, e.g., having a generally hill shape to partially fit into the diamond-shaped portion 20 on an opposite side of the engagement end of the locking pawl. The detent pawl may be provided to apply a sufficient force on the diamond-shaped portion 20 to allow the cutting burr 10 to be moved in and out of the surgical drill, while reducing the likelihood that the cutting burr will inadvertently fall out of the surgical drill when in a loading position.

As shown by the a comparison of the sectional views of the diamond-shaped portions 18 and 20 (FIGS. 5 and 6), the two diamond shapes may be different in size, where the diamond shape in diamond-shaped portion 18 is larger than the diamond shape of the diamond-shaped portion 20. As illustrated, the vertices 32 and 36 fall below the outer diameter of the shank 16 and both diamond shapes are in axial alignment with each other and may be oriented in parallel relationship. In some implementations, the diamond-shaped portion 20 and the diamond-shaped portion 18 may be the same size, or the diamond-shaped portion 18 may be larger than the diamond-shaped portion 20. In the various configurations, the vertices 26 and 32 of diamond-shaped portions 20 and 18, respectively, are along a same line and in a same plane as the center line A. Exemplary dimensions of the six-sided diamond diamond-shaped portions 18 and 20 are listed in degrees (°) and inches (″) and may be substantially as follows:

The angle of the facets of the six-sided diamond in the diamond-shaped portion 20–a=47°;

The width of the facets of the six-sided diamond in the diamond-shaped portion 20–b=0.046″;

The width of the facets of the six-sided diamond in the diamond-shaped portion 18–c=0.065″;

The width of the shank 16 at the space between diamond-shaped portions 18 and 20–d=0.029″;

The length of the diamond-shaped portion 20–e=0.068″; and

The length between the proximal end and the back wall of diamond-shaped portion 18 f=0.149″. This dimension may contribute to the feature of substantially reducing the axial play of the cutting burr.

Thus, in accordance with the above, the diamond-shaped portions 18 and 20 provide sufficient cross-sectional dimensions to meet strength and reliability requirements needed for high-speed, large force surgical applications. Facets 34 and 34a of the diamond shape 18 provide positive engagement surfaces in both clockwise and counter-clockwise rotational directions and are sufficiently sized to withstand rotations forces in either direction without wobbling within the surgical drill. For example, some surgical drills provide bi-directional rotation, allowing the surgeon to selectively reverse rotation for various surgical techniques. In conventional designs, there may be rotational play between a bit end and a drive portion. However, the symmetrical diamond facets 34 and 34a of the diamond-shaped portion 18 provide substantial drive surfaces in either direction.

With reference to FIGS. 7A and 7B, the diamond-shaped portion 18 at the outermost proximal end of the cutting burr 10 is designed to have unidirectional backward compatibility with older drill instruments in accordance with aspects of the disclosure. For example, a conventional drill instrument may include an insert 106 that defines a generally rectangular slot 105 having rounded side walls. The rounded side walls may be shaped with a radius of curvature that parallels the outer wall of the insert 106. Conventional cutting burrs may include a complementary generally rectangular portion having rounded side walls that is received by the slot 105. The insert 106 may be driven by a motor, thus providing rotational force on the cutting burr.

As shown in FIG. 7A, in accordance with some implementations, facets 34a and 34d of the diamond-shaped portion 18 engage the inner walls of the slot 105. The dimension c of the diamond-shaped portion 18, noted above, may be sized such that the surface area of the facets 34a and 34d is substantial enough to withstand the torque provided by the motor of the conventional drill instrument. Thus, the cutting burr 10 of the present disclosure may be utilized by conventional drill instruments.

Referring now to FIGS. 8A and 8B, in some implementations, the cutting burr 10 of the present disclosure provides for a level of self-alignment within the insert 106. The insert 106 may be provided in a compatible surgical drill and define a diamond-shaped key slot 107, a pointed shaped inlet end 109, and opposing holes 110 that formed in the insert 106 for receiving dowel pin which may serve to locate the cutting burr 10 when inserted into the key slot 107. The inlet end 109 serves to facilitate the alignment and insertion of the cutting burr 10 as it is advanced toward and into the key slot 107 of the insert 106. For example, if the diamond-shaped portion 18 is not in alignment with the key slot 107 (FIG. 8A), a bottom surface of the diamond-shaped portion 18 will contact an apex 111 of the inlet end 109 causing the cutting burr 10 to rotate into alignment with the key slot 107. As such, the cooperative engagement of the diamond-shaped portion 18 and inlet end 109 facilitates the easy insertion of the cutting burr 10 into the compatible surgical drill. As such, the diamond portion 18 serves to provide a secure connection in the key slot 107.

FIGS. 9, 10, and 11 illustrate different example cutting bits 22 provided at a distal end on the shank 16. As described above, the shank 16 may include the attachment portion 12. The cutting bits 22 may be milled or cut-out portions. The cutting burr 10 in FIG. 9 exemplifies a fluted ball or drill bit; the cutting burr 10 in FIG. 10 exemplifies a diamond ball; and the cutting burr 10 in FIG. 11 exemplifies a twist drill. The cutting bits 22 are presented only as examples and are not intended to limit the scope of the present disclosure as numerous variations are possible.

Thus, as described above, a cutting burr is provided with an attachment end that has a configuration and dimensions that serve to facilitate the insertion of the cutting burr into the surgical cutting instrument. When locked in the running position there is a structure that prevents the cutting burr from having any axial movement. Also, there is a positive connection such that the cutting burr rotates concentrically without any wobbling motion.

While particular aspects of the present subject matter described herein have been shown and described, it will be apparent to those skilled in the art that, based on the teachings herein, changes and modifications may be made without departing from the subject matter described herein and its broader aspects and, therefore, the appended claims are to encompass within their scope all such changes and modifications as are within the true spirit and scope of the subject matter described herein.

What is claimed:

1. A cutting burr comprising:
    a shank with an engagement feature at a proximal end of the shank sized and configured to receive rotational forces from a surgical drilling instrument and a cutting bit formed on a distal end of the shank,
    the engagement feature including four planar surfaces, where a first pair of the planar surfaces includes a first surface and a second surface that meet at a first apex, where a second pair of the planar surfaces includes a third surface and a fourth surface that meet at a second apex, where the first and the third surfaces are opposite and parallel each other and the second and the fourth surfaces are opposite and parallel each other, and
    an insert including a slot defined by substantially parallel opposing side walls and curved side walls extending between the parallel opposing side walls, where the engagement feature is received within the slot and a width of the slot measured between the opposing side walls corresponds to a width between the first surface and the third surface of the engagement feature such that shank cannot rotate within the slot when the shank is coupled to the insert.

2. The cutting burr of claim 1, wherein the insert is adapted to be inserted into a complementary shaped mating recess of a surgical drilling instrument,
    wherein engagement between the opposing side walls of the insert and the corresponding first or second pair of planar sides of the engagement feature provides rotational forces to the shank.

3. The cutting burr of claim 1, wherein a radius of curvature of the curved side walls corresponds to a radius of curvature of an outer wall of the insert.

4. The cutting burr of claim 1, wherein the first pair of the planar surfaces of the engagement feature is joined to the second pair of the planar surfaces by curved side edges, the first and fourth surfaces being joined by a first curved side edge and the second and third surfaces being joined by a second curved side edge,
    wherein the radius of curvature of the curved side walls of the slot corresponds to a radius of curvature of the first and second curved side edges of the engagement feature.

5. The cutting burr of claim 4, wherein a diameter of the slot defined at the curved side walls corresponds to a diameter defined between the first and second curved side edges of the engagement feature.

6. The cutting burr of claim 1, wherein the slot defines a diamond-shape in cross-section and is sized and configured to engage the first and second pairs of planar surfaces of the engagement feature.

7. The cutting burr of claim 1, wherein the insert further defines a pointed-shaped inlet end, where the inlet end facilitates an alignment and insertion of the cutting burr as it is advanced toward and into the slot,
    wherein, during coupling, contact between the proximal end of the shank and the pointed-shaped inlet end of the insert causes the shank to rotate thereby bringing the engagement feature into alignment with the slot.

8. The cutting burr of claim 7, wherein the pointed-shaped inlet end includes a first tapered surface extending from an outer surface of the insert towards a centerline of the insert and a second tapered surface extending from the outer surface of the insert towards the centerline of the insert opposite the first tapered surface.

9. The cutting burr of claim 1, wherein the insert includes a hole extending through a sidewall of the insert, where a dowel pin received within the hole locates the cutting burr and the engagement feature within the slot.

10. The cutting burr of claim 1, wherein the first and the third surfaces of the engagement feature have equal length measured around the circumference of the shank,
    wherein the second and fourth surfaces of the engagement feature have an equal length from the second length measured around a circumference of the shank.

11. The cutting burr of claim 1, wherein the width of the engagement feature measured between the first apex and the second apex is less than a diameter of the shank.

12. The cutting burr of claim 1, wherein the first apex and the second apex are in axial alignment.

13. The cutting burr of claim 1, wherein the engagement feature extends from the proximal end of the shank to a tapered surface extending from each of the four planar surfaces to an outer surface of the shank.

14. The cutting burr of claim 1, wherein the first pair of the planar surfaces is joined to the second pair of the planar surfaces around a circumference of the shank by curved side edges, the first and fourth surfaces being joined by a first curved side edge and the second and third surfaces being joined by a second curved side edge, and
    wherein the curved side edges have a radius of curvature corresponding to an outermost radius of curvature of the shank.

15. A surgical instrument including:

a surgical drilling instrument including a motor and a locking pawl;

a cutting burr releasably connected to the locking pawl and receiving rotational forces output from the motor, the cutting burr comprising:

a shank with an engagement feature at a proximal end of the shank sized and configured to receive rotational forces from the surgical instrument and a cutting bit formed on a distal end of the shank, the engagement feature including four planar surfaces, where a first pair of the planar surfaces includes a first surface and a second surface that meet at a first apex, where a second pair of the planar surfaces includes a third surface and a fourth surface that meet at a second apex, where the first and the third surfaces are opposite and parallel each other and the second and the fourth surfaces are opposite and parallel each other, and an insert including a slot defined by substantially parallel opposing side walls and curved side walls extending between the parallel opposing side walls, where the engagement feature is received within the slot and a width of the slot measured between the opposing side walls corresponds to a width between the first surface and the third surface of the engagement feature such that shank cannot rotate within the slot when the shank is coupled to the insert.

16. The surgical instrument of claim 15, wherein the four planar surfaces of the engagement feature are adapted to accept rotational engagement forces of the motor, wherein the locking pawl engages the cutting burr to fix an axial position of the cutting burr with respect to the surgical drilling instrument.

17. The surgical instrument of claim 15, wherein the first pair of the planar surfaces of the engagement feature is joined to the second pair of the planar surfaces by curved side edges, the first and fourth surfaces being joined by a first curved side edge and the second and third surfaces being joined by a second curved side edge, wherein a radius of curvature of the curved side walls of the slot corresponding to a radius of curvature of the first and second curved side edges of the engagement feature.

18. The surgical instrument of claim 15, wherein the slot defines a diamond-shaped slot sized and configured to engage the first and second pairs of planar surfaces of the engagement feature.

19. The surgical instrument of claim 15, wherein the insert further defines a pointed-shaped inlet end, and wherein the inlet end facilitates an alignment and insertion of the cutting burr as it is advanced toward and into the slot, wherein, during coupling, contact between the proximal end of the shank and the pointed-shaped inlet end of the insert causes the shank to rotate thereby bringing the engagement feature into alignment with the keyed slot, wherein the pointed-shaped inlet end includes a first tapered surface extending from an outer surface of the insert towards a centerline of the insert and a second tapered surface extending from the outer surface of the insert towards a centerline of the insert opposite the first tapered surface.

\* \* \* \* \*